United States Patent [19]

Osborg

[11] 4,013,758

[45] Mar. 22, 1977

[54] PROCESS FOR PREPARING HYDRAZINES

[76] Inventor: Hans Osborg, 80 Longview Road, Port Washington, N.Y. 11050

[22] Filed: Aug. 7, 1975

[21] Appl. No.: 602,837

[52] U.S. Cl. .............................. 423/407; 423/408; 260/569; 260/583 B

[51] Int. Cl.² ...................................... C07C 109/00

[58] Field of Search ........... 423/407, 408; 260/569, 260/583 B, 566 B

[56] References Cited

UNITED STATES PATENTS

| | | | |
|---|---|---|---|
| 2,806,851 | 9/1957 | Sisler et al. | 260/583 B X |
| 2,808,439 | 10/1957 | Barrett et al. | 260/569 |
| 3,050,560 | 8/1962 | Randolph et al. | 260/583 B |
| 3,281,211 | 10/1966 | Lacey | 423/408 |
| 3,657,324 | 4/1972 | Sheppard et al. | 260/569 |

*Primary Examiner*—G. O. Peters
*Attorney, Agent, or Firm*—Kane, Dalsimer, Kane, Sullivan and Kurucz

[57] ABSTRACT

A novel process is disclosed for preparing hydrazine, phenyl-substituted and alkyl-substituted hydrazines. The process comprises reacting an N-haloamine with the corresponding alkali metal or alkaline earth metal amide in the presence of a non-aqueous, inert carrier and at a temperature below about 0° C., briefly heating the resulting reaction mixture and separating the desired hydrazine product.

16 Claims, No Drawings

PROCESS FOR PREPARING HYDRAZINES

BACKGROUND OF THE INVENTION

1. Field of the Invention

The invention relates to a process for preparing hydrazine, phenyl-substituted and alkyl-substituted hydrazines.

2. Brief Description of the Prior Art

Hydrazine, phenyl-substituted and alkyl-substituted hydrazines, particularly unsymmetrical dimethylhydrazine, have become important commercial compounds for a wide variety of purposes, including as intermediates in the preparation of blowing agents, pharmaceuticals, fuels, agricultural products and the like.

Prior to my invention, a number of processes were known for the preparation of hydrazine and its alkyl-substituted derivatives. For example, the Raschig Process is a commercial synthesis of hydrazine from ammonia and sodium hypochlorite in two steps. Initially, chloramine is formed with sodium hydroxide by-product. Then the chloramine reacts with excess ammonia to form hydrazine. In the first stage, chloramine, is formed rapidly. However in the second step the reaction of chloramine with ammonia is slow and requires heat for completion. The rate of formation of the desired hydrazine increases with temperature. As a side reaction, the hydrazine reacts with the starting chloramine to form ammonium chloride and nitrogen. This is of course undesirable and to avoid a high rate of hydrazine decomposition, the process must be carried out at high temperatures (circa 130° C.) and in large excesses of ammonia (20:1 to 30:1) to minimize the reaction of hydrazine product with chloramine reactant.

The Olin process (Kobe et al., Advances in Petroleum Chemistry and Refining, Vol. 2, Interscience Pub. Inc., New York, N.Y., 1959, Chapter 9) is a modification of the Raschig process employing anhydrous ammonia. The anhydrous ammonia is injected under pressure into an aqueous chloramine solution and has the advantage wherein by the heat of dilution, the temperature of the reaction mixture is immediately raised to circa 130° C., i.e.; ideal reaction temperature for the reaction of the ammonia with the chloramine. However, heat must be provided from outside fuel sources to carry the reaction to completion and to separate the large volumes of ammonia in subsequent distillation steps. Further energy is required to remove sodium chloride and sodium hydroxide by-product and to recover the hydrazine. The hydrazine recovered is actually the monohydrate. To obtain the pure product (anhydrous) substantial further energy is required to drive off the chemically bound water.

The Schestakoff method is based on the degradation of urea by sodium hypochlorite to produce hydrazine. The reaction resembles the Hoffmann preparation of primary amines from amides. In the process, a cold aqueous solution of urea and sodium hydroxide is added to a cold aqueous solution of sodium hypochlorite. The heat of reaction increases the temperature to 100° C. where the reaction takes place at a fast rate. In the process, steam in large quantity must be used in the preparation of the urea solution (43% solution) to offset the huge endotherm of solution. The product, as in the Raschig process, is the monohydrate in low concentration (about 3%). Additional energy is required to concentrate, convert the hydrate and fractionate the final hydrazine product. Simultaneously, excessive quantities of alkali and alkali salts become useless by-products. (Ratio about 12:1 of by-products to $N_2H_4$ thus manufactured, by weight).

The Bergbau or Bayer process is not a commercial procedure although the heat requirements are not as great as in the above-described commercial processes. In the Bergbau or Bayer processes, ammonia is reacted with chlorine in the presence of a ketone to form an intermediate diazocyclopropane or ketazine. The intermediate is then hydrolyzed to the hydrazine hydrate and the latter converted to the desired anhydrous product. The same energy requirements are necessitated in recovering the hydrazine as for the commercial processes previously described.

Under the impact of the current energy crisis it has become of paramount importance to employ logistic reasoning, and to subject a manufacturing process to the requirements of logistics, as a matter of national necessity. Therefore, it becomes imperative to avoid, or at last minimize the use of energy in excess of thermodynamic requirements needed to complete a given reaction. In this connection, it must be borne in mind that the raw materials and auxiliary chemicals employed carry a liability into the process through the energy expended to produce such compounds before they are used for the present purpose; i.e.; NaOH, $Cl_2$, urea, $NH_3$, etc., consume energy in their manufacture. This energy liability must be entered into the overall equation in order to determine the degree of gain or loss in terms of energy required for the end product. Simultaneously, the weight ratio of by-products versus the desired end-product must be evaluated as an important factor in the overall logistics of a process. By the process of the present invention, minimal energy requirements are made providing advantages in economy and saving of national resources.

The prior art also recognizes the difficulty of isolating anhydrous hydrazine from a variety of prior art reaction mixtures; see U.S. Pat. Nos. 2,735,752 and 2,899,364. By the method of the present invention, anhydrous hydrazine is obtained, in high concentrations within the reaction mixture. The pure product is readily separated by conventional distillation technique.

A particular advantage of my process resides in the fact that it is particularly useful to prepare the alkyl-substituted hydrazines, especially unsymmetrical dimethylhydrazine. The advantages of the process of the invention are two-fold in regard to the preparation of unsymmetrical dimethylhydrazine (referred to hereinafter at times as "UDMH"). First, as noted above the energy crisis is imposing upon the technology of UDMH manufacture requirements which necessitates basic changes in methods in order to cope with the need to improve thermodynamic efficiencies and to reduce drastically, concomitant production of large amounts of waste products whose parent compounds consumed an unnecessary amount of energy in the first place (e.g., caustic soda and chlorine converted into large amounts of by-product sodium chloride). The commercially accepted method of preparing UDMH heretofore has comprised nitrosation of dimethylamine via its sulfuric acid salt and by means of sodium nitrite to obtain dimethylnitrosoamine. The latter compound is reduced to obtain the UDMH. The difficulty of this procedure has been found to include the energy requirements for starting materials and separation of desired product.

Second and perhaps of greater consequence is the hazard posed to operating personnel by the dangerous nitrosoamine intermediates employed in preparing UDMH. Dimethylnitrosoamine is a highly active carcinogen. The Occupational Safety and Health Authority (OSHA) has imposed strict rules to control manufacturing procedures and processes wherein any nitrosamine is used or produced. In the currently used commercial method for preparing UDMH, the following have been found to be particularly troublesome.

1. Large quantities of sodium sulfate contaminated with nitroso compound whose isolation and/or recovery from the waste sulfate has not been possible in any manner compatible with present health protection standards.

2. Difficulty of handling the nitroso compound produced without exposure of workers.

3. Inadequate conversion of the nitroso compound to the hydrazine generating additional nitroso compound residues which constitute a hazard and are difficult to treat, convert, or dispose of.

4. In the end, the hydrazine thus produced, has to be fractionated or distilled to bring it up to specifications. Even in this final step residual nitroso compound have to be dealt with.

It is therefore not surprising that a general review of the patent literature indicates a concentration on how to convert the nitroso compounds to hydrazine and UDMH.

By the method of my invention, high yields of hydrazine and alkyl-substituted hydrazines are obtained, under conditions offering little or no hazards to operating personnel and the environment. The method advantageously employs the most saving means of our national resources including energy.

SUMMARY OF THE INVENTION

The invention comprises a process for preparing compounds of the formula:

(I)

wherein R and R' are each selected from hydrogen, phenyl and lower alkyl, provided that when one of R and R' is phenyl, the other of R and R' is hydrogen, which comprises;

a. reacting together substantially equimolar proportions of the corresponding haloamine compound of formula:

(II)

wherein X is selected from chlorine and bromine, R and R' are each selected from the group consisting of hydrogen and lower alkyl; and a corresponding amide selected from an alkali metal amide and an alkaline earth metal amide, at a temperature of from about 0° C. to about −50° C. and in the presence of a non-aqueous, inert carrier which is a liquid at temperatures within the range of from about −110° C. to about 200° C.; and b. separating the product compound (I) from the resulting reaction mixture.

The term "lower alkyl" is used herein to mean alkyl of from 1 to 6 carbon atoms, inclusive. Representative of lower alkyl are methyl, ethyl, propyl, butyl, pentyl and hexyl including isomeric forms thereof.

The term "alkali metal" is used herein in its normally accepted sense as embracive of lithium, sodium, potassium, rudidium and cesium.

The term "alkaline earth metal" is used herein as embracive of magnesium, calcium, barium and strontium.

The term "non-aqueous, inert carrier" as used throughout the specification and claims means a liquid solvent or carrier vehicle for the reactants employed herein and which does not enter into or otherwise adversely effect the desired course of the reaction and which is substantially free of water. By "substantially free of water" I mean having less than 1% by weight water, preferably less than 0.1%. Illustrative of such carriers are dried kerosene (preferably of low sulfur content and freshly distilled), anhydrous ammonia, dialkylamines such as dimethylamine, trialkylamines such as tripropylamine and tributylamine and tetraalkyl diamines such as N,N,N',N'-tetramethyl-1,3-butanediamine, mixtures thereof and the like. A particularly preferred inert carrier in the process of the invention for preparing unsymmetrical dimethylhydrazine is dimethylamine.

DETAILED DESCRIPTION OF THE INVENTION

The process of the invention is carried out by reacting substantially equimolar proportions of the compounds (II) and an alkali metal amide or an alkaline earth metal amide. The reaction is illustrated by the schematic formula:

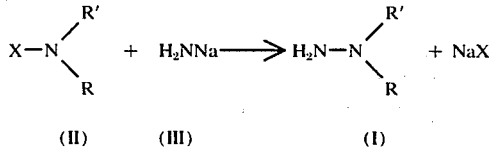

wherein X, R and R' are as previously defined and sodamide (III) is used to illustrate an alkali metal or alkaline earth metal amide.

By the term "substantially equimolar" as used throughout the specification and claims, it is meant that the proportions of haloamine reactant (II) and alkali metal or alkaline earth metal amide are within ±5 percent of being equimolar. Preferably, the proportions are exactly equimolar.

The reaction, described in the above reaction scheme is carried out advantageously at atmospheric pressures although super-atmospheric pressures may be employed to speed reaction, improve yields or to facilitate the use of a carrier which would otherwise ordinarily not be a liquid at the temperature selected for carrying out the reaction.

The process of the invention is carried out by first bringing the reactants together at a temperature within the range of from 0° to −50° C., preferably from −20° to −50° C. and when the inert carrier is anhydrous ammonia, preferably from −30° to −35° C. in order to build up a concentration of the product of formula (I) rapidly and without extensive side reactions. At the prescribed temperature, reaction generally occurs immediately or at least within several minutes. The reaction is generally slower when the inert carrier is solely ammonia. Progress of the reaction may be observed by employing conventional analytical instruments to determine the disappearance of reactants and the appearance of product of the formula (I).

After the reaction is in progress (generally after about a 20% yield has been obtained), the reaction mixture may be warmed to complete the reaction more rapidly. Unexpectedly, after the reaction is underway, heating the reaction mixture up to reflux temperatures for a short period (10 minutes to several hours) will complete the reaction very rapidly.

The haloamine reactant (II) and the amide reactant may be brought together by any convenient means and in any sequence of addition so long as admixture is rapid. For example, one or both haloamine reactant (II) and the amide reactant may be admixed first with inert carrier and then brought together in admixture. Preferably the amide reactant is dissolved or slurried in the inert carrier and the haloamine reactant (II) added thereto. The resulting reaction is exothermic and the reaction mixture must be cooled to maintain the desired temperature. To assist in maintaining a low temperature the reactants may be brought together slowly to avoid raising the temperature of the reaction mixture rapidly, beyond the desired limits. Advantageously the reactants are cooled to the desired temperature prior to being brought together.

The reaction which comprises the process of the invention is generally initiated almost immediately after the reactants are brought together. The desired hydrazine product (I) may then be separated from the reaction mixture as it forms employing conventional apparatus or the reaction may be allowed to proceed to completion before separating the desired product (I). To complete the reaction more rapidly, the reaction mixture may be allowed to slowly warm to room temperature after the reaction has progressed to partial completion. While warming, the reaction mixture is observed for a heat surge and if such occurs, (indicating the reaction is not progressing as desired), the reaction mixture should be immediately cooled again to below 0° C. for a brief period and then allowed to slowly warm again. The rate of temperature rise allowed is dependent on the uniformity of temperature use. If the temperature "spikes" upward during warming the reaction is not proceeding properly or controlled to permit warming above about 0° C. If the temperature rise profile is smooth or uniform, the reaction mixture may be warmed to 0° C. more rapidly. Once the reaction mixture has been warmed to about 0° C. and no surges or temperature "spikes" appear, the rise to room temperature should be rapid. If desired, heating to reflux temperature for a short period to complete the reaction should also be at a rapid rate. Generally no more than 5 to 15 minutes are required at reflux temperature to assure favorable yields without undue expenditure of energy. When the inert carrier employed is ammonia, the ammonia may be allowed to vaporize during warming and is recovered by conventional techniques. The residue which comprises hydrazine (I) and chloride by-product may then be separated by conventional technique, i.e.; by filtration, crystallization and distillation.

When the inert carrier employed is other than ammonia, the reaction mixture may be warmed to room temperature as described above and then is preferably heated rapidly to reflux temperature for from 5 to 15 minutes. Longer periods of refluxing may be used to increase yields further, but any advantage in yield gains should be weighed against the increase in energy expenditure. At the end of this refluxing period, the reaction mixture may be quickly chilled to precipitate the chloride by-product. The chilled reaction mixture is then filtered to remove the chloride precipitate and the filtrate distilled to separate the hydrazine product (I). Alternatively, at the completion of refluxing, the hydrazine (I) may be distilled directly from the reaction mixture in good yields.

In a preferred embodiment process of the invention, the reactant amide and haloamine (II) are introduced together in a reaction zone and then the hydrazine reaction product (I) is immediately swept clear of the reaction zone before admixture with additional starting material occurs. This prevents undesired side reactions and raises yields considerably. It is important in such a procedure that the feed rate of the haloamine reactant (II) and the amide reactant be controlled to provide equimolar proportions so as to avoid undesirable side reactions. For example, when the product (I) is hydrazine, a molar excess of sodamide reactant (III) will react with the desired hydrazine product to form sodium hydrazid and ammonia. In the alternative, a molar excess of haloamine reactant will react disproportionately to form sodium salt, nitrogen and ammonium salt. To avoid such side reactions and a consequent lower yield, the desired product of formula (I) is immediately removed as formed from the reaction zone and the possibility of reaction with the starting reactants.

Removal of the desired hydrazine product (I) from the presence of starting reactants may be accomplished most conveniently by carrying out the reaction in a continuous, pipeline type reactor of the type well known in the art. The process is carried out by introducing the haloamine reactant (II) and amide reactant into an inert carrier (or with an inert carrier) at the reaction zone of the reactor and carrying the resulting hydrazine product (I) away to a non-feed zone almost immediately. Advantageously the inert carrier sweeps the product hydrazine (I) from the reaction zone within about 30 seconds. The removed product hydrazine (I) in carrier may then be allowed to warm to ambient temperatures. The hydrazine product (I) may then be separated from the reaction mixture by conventional methods and techniques such as by distillation. Alternatively, the product hydrazine (I) may be simultaneously swept from the reaction zone of the reactor and distilled from the carrier, to obtain even higher product yields. The rate of bringing the reactants together may be any rate consistent with the speed of the particular reaction being carried out. The zones of the pipe following the initial reaction zone may be provided with heating means to bring the reaction mixture to room temperature or above after the product (I) is formed for the purposes described previously, i.e.; shortening the period of time to complete the reaction. The pipe-line reactor may also be adapted to deposit the product (I), in inert carrier, into a cooling or distillation vessel for separation of the product as described previously.

Those skilled in the art will appreciate that the process of the invention may be carried out in batch technique or, preferably by a continuous procedure. In a continuous procedure, the reactants may be admixed with inert carrier and chilled to a temperature below about 0° C. The chilled reactants may then be introduced to each other in a reaction zone maintained at a temperature below about 0° C. for any desired length of time as previously described. The reaction mixture may then be heated in the same reaction zone or transferred to a warming zone to complete the reaction and separate inert carrier. The inert carrier, such as ammonia may then be recycled to mix with fresh reagent and the desired hydrazine product further purified by distillation and like methods. The by-products, such as sodium chloride may also be separated and recovered for their value.

By the process of the invention, the ratio of product to waste or by-product is extremely high, i.e.; on the order of about 1:1.25. This is unexpected in view of the theoretical ratio being 1:1.

The reactant haloamine compounds of formula (II) described above and used in the process of the invention are generally well known as is their preparation. Representative of such compounds (II) are chloramine, chloromethylamine, chlorodimethylamine, chloroethylamine, chlorodiethylamine, chloropropylamine, butylchloroamine, chlorodibutylamine, amylchloroamine, chlorodihexylamine and the like.

The alkali metal amides and alkaline earth metal amides used as reactants in the process of the invention when R and R' in the product of formula (I) are selected from hydrogen and lower alkyl are also generally well known as is their preparation. Representative of such alkali metal amides are sodamide, lithium amide, potassium amide and the like. Although higher yields may be obtained by use of potassium amide, sodamide is preferred in the process of the invention because of its lower cost and greater abundance. The alkaline earth metal amides are represented by calcium amide, barium amide and the like.

When one of R and R' in the product of formula (I) is phenyl, the amide reactant may be the alkali metal anilino such as, for example, sodium anilide. In the process for preparing phenylhydrazine, the most preferred inert carrier is xylene or dimethylaniline.

The inert carrier most advantageously employed in the process of the invention is a non-aqueous, inert solvent for the amide reactant and which is a liquid within the temperature range of from about −95° C. to about 180° C., preferably from about −40° to 160° C. Inert organic solvents such as dimethylamine, tripropylamine, kerosene, N,N,N',N'-tetramethyl1,3-butanediamine, liquid anhydrous ammonia and the like are representative of the preferred inert carriers used in the process of the invention.

The proportion of inert carrier employed is not critical. Advantageously the proportion of carrier is from about 50 to about 1000 percent by weight of the amide reactant.

The following examples describe the manner and process of making and using the invention and set forth the best mode contemplated by the inventor of carrying out the invention but are not to be construed as limiting.

EXAMPLE 1

A 5 liter, three neck (ball joint) round bottom flask equipped with means for stirring, thermometer, condenser, dropping funnel and means for cooling and heating is purged of air with nitrogen gas and charged with 1750 grams of anhydrous liquid ammonia. While maintaining the charge at a temperature of −30° to −35° C., 126 grams of sodamide is added with stirring. To the resulting mixture there is added 165 grams of chloramine dissolved in 500 grams of tripropylamine and chilled to a temperature of −20° C. The addition is dropwise over a 40 minute period of time while maintaining the temperature below −20° C. and under atmospheric pressures. At the end of this period, stirring of the reaction mixture is continued for an additional 20 minutes. The reaction mixture is then allowed to warm over a period of 20 minutes to room temperature. In the first 10 minutes there is strong refluxing and in the last 10 minutes ammonia vaporizes and is distilled off. The residue is refluxed for 10 minutes at temperatures of 100°–120° C. and fractionally distilled at a temperature of 110° to 120° C. to obtain 47 gms (50% of theory) of hydrazine.

Similarly, following the above procedure but replacing the chloramine as used therein with an equal proportion of chloromethylamine, and chlorodibutylamine respectively, there is obtained monomethylhydrazine and unsymmetrical dibutylhydrazine respectively.

EXAMPLE 2

Following the procedure of Example 1, supra., but refluxing the reaction mixture for 10 hours instead of 10 minutes as carried out therein, 63 gms (65% of theory) of hydrazine is obtained.

EXAMPLE 3

Following the procedure of Example 1, supra., but by also adding 500 grams of tripropylamine to the charge of anhydrous ammonia it is found that the charge refluxes at circa −20° C. and there is obtained 58 grams (60% of theory) of hydrazine. It is observed that the mixture of inert carriers noticeably improved the yield of hydrazine product.

EXAMPLE 4

Following the procedure of Example 3, supra., but replacing the chloramine as used therein with an equal molar proportion of dimethylchloramine, there is obtained 108 grams (60% of theory) of unsymmetrical dimethylhydrazine.

EXAMPLE 5

The apparatus of Example 1 is purged with ammonia and then charged with 1750 grams of anhydrous liquid ammonia and 125 grams of sodamide slurry in 500 gms of tributylamine. The charge is held to a temperature of circa −20° C., 280 grams of dimethylchloramine mixed with 500 grams of tributylamine are chilled to −20° C. and added dropwise over a period of about 40 minutes with stirring while maintaining the reaction mixture temperature at circa −20° C. At the completion of addition, the reaction mixture is stirred for 10 hours and then allowed to warm to room temperature. During this period, ammonia vaporizes and is removed by distillation. The residue is heated to refluxing temperature at a temperature of circa 100° to 120° C. The resulting mixture is then fractionally distilled at a temperature of circa 63°–64° C. to obtain 135 grams (75% of theory) of unsymmetrical dimethylhydrazine.

EXAMPLE 6

The apparatus of Example 1 is purged of air with nitrogen gas and then charged with about 1720 gms. of tripropylamine and 126 gms of sodamide. The resulting slurry is cooled to about −20° C. and then saturated with anhydrous liquid ammonia. While maintaining the cold temperature, 280 grams of dimethylchloramine in 500 gms. of tripropylamine is added with stirring, dropwise over a period of about 40 minutes. At the end of addition, the mixture is stirred for about 20 minutes and then allowed to warm to room temperature over a period of 20 minutes. During this period, ammonia is distilled off. The residue is refluxed for about 10 minutes. The resulting mixture is then distilled at 55° to 70° C. and the distillate redistilled at 62° to 66° C. to obtain 126 grams (70% of theory) of unsymmetrical dimethylhydrazine.

EXAMPLE 7

Following the procedure of Example 6, supra., but replacing the tripropylamine as used therein with N,N,N',N'-tetramethyl-1,3-butanediamine and holding at −20° C. for 10 hours instead of 10 minutes as carried out therein before refluxing. 162 grams (90% of theory) of unsymmetrical dimethylhydrazine is obtained.

EXAMPLE 8

The apparatus of Example 1 is charged with 2000 grams of dimethylamine and 126 grams of sodamide. The resulting slurry is thoroughly agitated while the reaction vessel is purged of air with nitrogen gas. The slurry is cooled to circa −20° C. while being saturated with liquid ammonia. 280 grams of dimethylchloramine in 500 grams of dimethylamine is added with stirring over a period of about 40 minutes. Upon completion of the addition, the reaction mixture is refluxed for about 50 minutes within a temperature of from 0° C. to room temperature. The resulting mixture is then distilled to remove dimethylamine. The residue is distilled under reduced pressure to separate the desired hydrazine in yields of 30 to 50%.

EXAMPLE 9

The apparatus of Example 1 is purged with nitrogen gas and charged with 2000 grams of white (distilled over sodium) kerosene and 126 grams of sodamide. The charge is saturated with ammonia and cooled to −20° C. To the cold mixture, 280 grams of dimethylchloramine in 500 grams of distilled kerosene (chilled to circa −20° C.) is slowly added (dropwise) over a period of 40 minutes. At the end of this period, the reaction mixture is allowed to warm to room temperature over a period of about 20 minutes. During this period, ammonia is distilled off. The residue is then refluxed for about 10 minutes after which the desired unsymmetrical dimethylhydrazine is separated by distillation.

EXAMPLE 10

The apparatus of Example 1 is purged of air with nitrogen gas and then charged with 2000 gms of xylene and 441 grams of sodium anilide. While maintaining the charge at a temperature of circa −20° C. it is saturated with ammonia liquid. Then 165 grams of chloramine dissolved in 500 grams xylene and chilled to a temperature of −20° C. is added dropwise to the slurry charge over a period of about 40 minutes with constant stirring. At the end of this period, the reaction mixture is stirred for 20 minutes and then allowed to warm to room temperature over a period of about 20 minutes. During this latter period, ammonia distills off. After the refluxing period, the residue is chilled to a temperature of circa 20° C. and filtered to remove precipitates. The filtrate and the precipitates are then fractionally distilled under reduced pressure to obtain phenylhydrazine.

Similarly, following the above procedure but replacing the xylene as used therein with an equal proportion of dimethylaniline, phenylhydrazine is obtained.

EXAMPLE 11

Each of the Examples 6–10, supra., is repeated but without saturating the charge with liquid ammonia. In each instance the desired hydrazine product of the formula (I) is obtained but the yields are from 10 to 25 percent by weight lower than when carried out in the presence of ammonia saturation of the carrier liquid.

What is claimed is:

1. A process for preparing hydrazines of the formula:

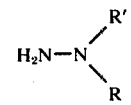

wherein R and R' are each selected from hydrogen, phenyl and lower alkyl, provided that when one of R and R' is phenyl, the other of R and R' is hydrogen, which comprises;
   a. providing a reaction mixture consisting essentially of equimolar proportions of the corresponding amine compound of formula:

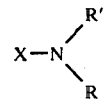

wherein X is selected from chlorine or bromine; a corresponding amide selected from the group consisting of an alkali metal amide and an alkaline earth amide; and from about 50 to about 1,000 percent by weight of the amide, of an inert, non-aqueous carrier solvent for at least one of said amide and said amine, which is a liquid at temperatures within the range of from about −110° to about 200° C.;
   b. reacting said amine compound with said amide compound in said reaction mixture, at a temperature of from 0° to about −50° C.; and
   c. separating the desired hydrazine compounds from the resulting reaction mixture.

2. A process according to claim 1 wherein R is hydrogen and R' is phenyl.

3. A process according to claim 1 wherein R and R' are each hydrogen.

4. A process according to claim 1 wherein R and R' are each methyl.

5. A process according to claim 1 wherein said reacting is initiated at a temperature of from about −20° to −35° C. and said carrier is anhydrous ammonia.

6. A process according to claim 1 wherein said carrier is kerosene.

7. A process according to claim 1 wherein said carrier is tripropylamine.

8. A process according to claim 1 wherein said carrier is anhydrous liquid ammonia.

9. A process according to claim 1 wherein said carrier is N,N,N',N-tetramethyl-1,3-butanediamine.

10. A process according to claim 3 wherein said carrier is dimethylamine.

11. A process according to claim 1 wherein said separating is by distillation.

12. A process according to claim 1 wherein said amide is sodamide.

13. A process according to claim 1 wherein said amide is selected from the group consisting of potassium amide, lithium amide and sodamide.

14. A process according to claim 13 wherein said amide is potassium amide.

15. A process according to claim 13 wherein said amide is lithium amide.

16. A process according to claim 1 wherein after reacting at a temperature of from 0° to about −50° C., the reaction mixture is allowed to warm to 0° C. and is then heated rapidly to a temperature up to reflux temperature.

* * * * *